United States Patent [19]

Rose

[11] Patent Number: 4,599,192

[45] Date of Patent: Jul. 8, 1986

[54] WOOD-TREATING COMPOSITION

[75] Inventor: John T. Rose, Charlotte, N.C.

[73] Assignee: Mineral Research and Development Corp., Charlotte, N.C.

[21] Appl. No.: 525,882

[22] Filed: Aug. 24, 1983

[51] Int. Cl.$^4$ ........................... A01N 9/20; A01A 9/24
[52] U.S. Cl. .................................... 252/383; 514/525; 424/137; 427/297; 427/440
[58] Field of Search ................ 252/383; 424/304, 137; 427/297, 440

[56] References Cited

U.S. PATENT DOCUMENTS

| | | | |
|---|---|---|---|
| 3,080,212 | 3/1963 | Oberley et al. | 427/44 |
| 3,290,353 | 12/1966 | Battershell et al. | 260/465 G |
| 3,331,735 | 7/1967 | Battershell et al. | 424/304 |
| 3,416,933 | 12/1968 | Nicholson et al. | 106/18.12 |
| 3,948,636 | 4/1976 | Marks | 71/112 |
| 3,968,239 | 7/1976 | Ferguson | 424/304 |
| 4,177,288 | 12/1979 | Gohlke | 424/294 |
| 4,303,668 | 12/1981 | Hasegawa et al. | 424/279 |
| 4,313,976 | 2/1982 | Leach | 427/297 |

OTHER PUBLICATIONS

Diamond Shamrock Product Bulletin on Nopcocide N-40-D, dated 2/81.
Diamond Shamrock Product Bulletin on Nopcocide N-96, dated 5/78.
EPA-Approved Label for STA-BRITE D, showing Mar. 1, 1982 as the date of EPA acceptance of this label.

*Primary Examiner*—Morton Foelak
*Assistant Examiner*—M. L. Moore
*Attorney, Agent, or Firm*—Timothy R. Kroboth

[57] ABSTRACT

A wood-treating composition useful for the control of surface molds and as a wood preservative is provided. The composition includes a certain fungicide effective to protect wood against surface molds and compatible with chromated copper arsenate, a wood preservative. Also provided is treated wood having the fungicide and the wood preservative applied thereto.

16 Claims, No Drawings

4,599,192

WOOD-TREATING COMPOSITION

TECHNICAL FIELD

This invention relates to a composition useful for the treatment of wood. More particularly, this invention relates to a wood-treating composition useful for the control of surface molds and as a wood preservative, and also relates to treated wood having applied thereto a wood preservative and a compound providing protection against surface molds.

BACKGROUND ART

Occasionally, under a combination of circumstances, a growth of black, dark brown, or whitish-gray mold appears on the surface of treated lumber, usually when treatment has been made under warm and humid conditions and the pressure treated lumber has been stored and/or shipped in closepiled stacks with no air ventilation to allow for drying. It does not normally occur on lumber dried to at least outer surfaces of 20–25% moisture content or below. The common molds are generally known as Asperqillus, Penicillium, Trichoderma species and Pullularia species. Chromated copper arsenate (CCA) is a known wood preservative that is ineffective against these surface molds.

Chromated copper arsenate is a highly acidic, strongly oxidizing material that is difficult to combine with organic compounds. In this regard, U.S. Pat. No. 3,080,212 to Oberley et al describes, at column 1, lines 64–72, the reaction of reducing sugars with CCA to form difficulty soluble salts as sludge or precipitate, and U.S. Pat. No. 3,416,933 to Nicholson et al discusses, at column 2, lines 30–34, certain wax emulsions that were too unstable in the presence of CCA to be of practical use. Also reactive with CCA are organic fungicides such as sodium pentachlorophenate. Reactivity of organic compounds with CCA can contribute to working solution sludge, and to precipitate deposits on treated wood. Working solution sludge can result even if wood is treated with a CCA-reactive organic compound such as an organic fungicide, long before CCA application.

Chromated copper arsenate has been found to be compatible with certain types of organic compounds. In U.S. Pat No. 4,313,976, CCA is combined with a benzene or naphthalene derivative compound having hydroxy, amino or sulfonic acid functional groups attached to a ring carbon atom. In the Nicholson et al patent, CCA is combined with a hydrophobic wax and a non-ionic surface active agent typically of the long chain fatty alcohol ethylene oxide condensate-type or of the alkyl phenol ethylene oxide condensate-type.

Certain halogenated benzene dinitriles are useful as fungicides on plants, fungus-infested soil, or fungal spores. This art is exemplified by U.S. Pat. Nos. 3,290,353 to Battershell et al, 3,331,735 to Battershell et al, 3,948,636 to Marks, 3,968,239 and 4,177,288, with 3,290,353 broadly describing fungicidal use on "other material to be protected." In U.S. Pat. No. 4,303,668 to Hasegawa, a halogenated benzene dinitrile in combination with an antibacterial and antifungal agent that is dehydroacetic acid, sorbic acid or the alkali metal salts, is said to have a number of fungicidal uses such as on wood (column 4, lines 11–19). In a Diamond Shamrock Product Bulletin on Nopcocide N-40-D (tetrachloroisophthalonitrile), use of a halogenated benzene dinitrile in aqueous paint systems is described. This bulletin also mentions stability of a particular halogenated benzene dinitrile in acidic aqueous media.

However, this art and all prior art of which I am aware, does not show that CCA is compatible with an organic nitrile, in particular with a biodegradable halogenated benzene dinitrile that I have found to be useful in protecting wood against surface molds, and thus fails to provide a wood-treating composition effective against surface molds, containing CCA in combination with a halogenated benzene dinitrile, and further fails to provide treated wood having applied thereto CCA and a halogenated benzene dinitrile.

SUMMARY OF THE INVENTION

It is accordingly an object of the present invention to provide a wood-treating composition containing CCA wood preservative in combination with a biodegradable halogenated benzene dinitrile effective against surface molds.

It is a further object of the present invention to provide treated wood having applied thereto CCA wood preservative in combination with a biodegradable halogenated benzene dinitrile effective against surface molds, and free of precipitate deposits caused by reaction between CCA and the fungicide.

Additional objects, advantages and novel features of the invention will be set forth in the description which follows, and in part will become apparent to those skilled in the art upon examination of the following or may be learned by the practice of the invention.

To achieve the foregoing objects and in accordance with the purpose of the present invention, as embodied and broadly described herein, there is provided a wood treating composition useful for the preventive control of surface molds and as a wood preservative. This composition includes an amount of a halogenated benzene dinitrile effective to protect wood against surface molds when applied to wood, and a concentration of chromated copper arsenate effective as a wood preservative when applied to wood. The halogenated benzene dinitrile is of the general formula set forth below. This wood-treating composition is free of working solution sludge caused by reaction between CCA and the fungicide.

Also provided by the present invention is treated wood having applied thereto an amount of chromated copper arsenate effective as a wood preservative, and having applied in direct surface contact with the surface of the wood, an amount of the halogenated benzene dinitrile effective to protect against surface molds. The treated wood is free of precipitate deposits caused by reaction between CCA and the fungicide.

DETAILED DESCRIPTION

In the present invention, the combination of a fungicide and a wood preservative is utilized to protect wood against undesirable mold growth on the surface of wood, and against deterioration and/or damage caused by, for example, termites, ascomycetes, brown rot, dry rot and white rot. As explained earlier, chromated copper arsenate, a wood preservative, is ineffective in protecting wood against surface molds. Moreover, chromated copper arsenate is a highly acidic, strongly oxidizing material, and is therefore difficult to combine with organic compounds. However, I have discovered that chromated copper arsenate is compatible with certain biodegradable halogenated benzene dinitriles, which I have also found to have efficacy in protecting wood against surface molds.

The essential components of the wood-treating composition of the present invention include chromated copper arsenate, and a particular halogenated benzene dinitrile of the general formula

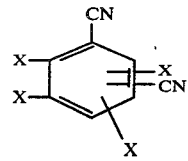

in which each X is hydrogen or halogen, i.e., chlorine, fluorine and bromine, with at least one X being halogen. These dinitriles are more commonly designated in the art as phthalonitriles, isophthalonitriles and terephthalonitriles. Compounds within this class, which are useful herein include tetrachloroterephthalonitrile, tetrafluoroterephthalonitrile, tetrachloroisophthalonitrile, difluorodichloroterephthalonitrile, 5-chloro-2,4,6-trifluoroisophthalonitrile, 2,3-dichloroterephthalonitrile and chlorotrifluoroterephthalonitrile. Other compounds within this class, which are useful herein, include the compounds specifically mentioned at column 1, lines 40-56, of U.S. Pat. No. 3,331,735, this disclosure being hereby incorporated by reference into this description. A preferred halogenated benzene dinitrile useful in my wood-treating composition is tetrachloroisophthalonitrile.

The halogenated benzene dinitrile is prophylactically effective against surface molds. Surface molds may be caused by fungi such as *Aspergillus flavus*, *Aspergillus niger*, *Penicillium expansum*, *Pullularia pullulans* and *Trichoderma sp.*

Another essential constituent of the wood-treating composition of my invention is chromated copper arsenate, which is made up of chromic acid, cupric oxide and arsenic pentoxide. Chromated copper arsenate, which protects wood against termites, ascomycetes, brown rot, dry rot and white rot, is conveniently available for formulating the wood-treating composition as CCA-A, CCA-B, and CCA-C. CCA-A is a 60% concentrate of chromated copper arsenate containing 39.30% $CrO_3$, 10.80% CuO and 9.90% $As_2O_5$. CCA-B is a 40% concentrate of chromated copper arsenate containing 15.1% $CrO_3$, 7.3% CuO and 17.6% $As_2O_5$. CCA-C is a 50% concentrate of chromated copper arsenate containing 22.40% $CrO_3$, 8.60% CuO and 19.00% $As_2O_5$. CCA-C is particularly useful for formulating my wood-treating composition. CCA-A, CCA-B and CCA-C are products of Mineral Research & Development Corporation, with CCA-C being available under the brandname OXCEL ® WOOD PRESERVATIVE.

The halogenated benzene dinitrile is employed in the composition of the present invention in an amount sufficient to protect wood treated with my composition, against surface molds. The amount of this ingredient may vary widely and is generally determined by a number of factors such as the ppm of the halogenated benzene dinitrile desired to be applied to the wood, with the ppm desired depending upon considerations such as the expected storage conditions of the treated wood. The wood could, for example, have on the order of about 150 to 780 ppm of the benzene dinitrile applied thereto. Useful amounts of the benzene dinitrile in the wood-treating composition of the present invention include amounts ranging from about 40 ppm up to and including about 16,000 ppm, and perhaps even higher. However, in the event that incompatibility may exist with CCA in some amount higher than 16,000 ppm, then it is to be understood, of course, that the amount of the benzene dinitrile is limited to an amount compatible with CCA. Under extremely hot and humid storage conditions, the benzene dinitrile is used in the wood-treating composition in a relatively higher amount than otherwise. Suitably, the benzene dinitrile is present in the composition at a level in the range of about 40 to 400 ppm. It is also to be understood that level of the benzene dinitrile being discussed herein is the amount of the compound present at the start of treatment, since the compound filters out on the wood surface. Thus, the wood-treating composition will have a lower level of the benzene dinitrile contained therein, at the end of treatment.

The composition of the present invention contains the CCA in a concentration effective to function as a wood preservative when applied to wood. CCA is used conventionally for this purpose, and this concentration is to be understood to be also conventional. Conveniently, the composition may contain the CCA in a concentration of about 1.1% CCA-C oxide.

Typically, wood is treated with my composition by using a pressure vacuum method of applying CCA wood preservative by the standard procedure prescribed by the American Wood Preservers Association. When this method is used, the CCA is impregnated throughout the wood. However, the benzene dinitrile is a dispersion of particles that filter out on the wood surface so as to be applied in direct surface contact with the surface of the wood.

Attention is invited to the below chart, which shows the pints of a concentrate of the benzene dinitrile (40.4% benzene dinitrile active ingredient mixed with 59.6% inert ingredients) required per 100 gallons of CCA treating solution to provide the concentration indicated.

| Conc. by Weight | 0.01% | 0.025% | 0.05% | 0.10% |
|---|---|---|---|---|
| Pts./100 gals. | 0.065 | 0.163 | 0.326 | 0.65 |

It is to be understood that this data is based on treating Southern yellow pine and 3.5 gals./ft.$^3$ retention of CCA treating solution. Thus, if for example, treating solution retention is less such as 3.2 gals./ft.$^3$, then 0.178 pts./100 gals., rather than 0.163 pts./100 gals., should be used.

My wood-treating composition is useful for protecting wood such as fresh cut or unseasoned wood, and lumber. An exemplary kiln dried charge is Southern pine having about 13-14% moisture and about 14% heartwood.

As indicated, unlike the CCA, the benzene dinitrile is insoluble in the aqueous-based treating solution and will thus settle out on prolonged standing. Thus, the treating solution should be agitated during the treatment of wood stock material. If desired, a compatible suspending agent may be added to the treating solution to retard or eliminate settling. By the term "compatible", I mean compatibility with a concentration of CCA useful in my wood-treating composition, and it is in this manner that I have used the term throughout this description and the claims set forth below. It also may be desirable to include in the wood-treating composition of the present invention a compatible defoamer, particularly where a relatively high level of the benzene dinitrile, i.e. 4000 ppm or more, is employed in the composition.

Also provided by the present invention is treated wood to which there has been applied an amount of the benzene dinitrile effective to protect against surface molds, and to which there has been applied an amount of the CCA having efficacy as a wood preservative. The amount of the CCA is, of course, conventional in the art. Useful amounts of the benzene dinitrile include amounts ranging from about 150 to 780 ppm, with higher or lower ppm being appropriate depending upon factors such as the expected storage conditions.

An alternative method of providing the treated wood of the present invention is to use dip application of the benzene dinitrile either before or after CCA pressure treatment. The same amount of the benzene dinitrile will generally be used in a treating solution for dip application, as would have been used in the wood-treating composition of the present invention. Dip application before CCA pressure treatment is to control mold while wood is air drying. The CCA pressure treatment may be done immediately following the dip treatment if desired. Dip application of the benzene dinitrile after CCA pressure treatment, may be done as soon after pressure treatment as desired. This alternative method of providing the treated wood also results in the benzene dinitrile being applied in direct surface contact with the surface of the wood. Any other method of applying the benzene dinitrile that achieves this result, such as spraying, may, of course, be used.

In the Examples which follow and throughout this description and the claims set forth below, all percentages are by weight unless otherwise specified.

EXAMPLE 1

Formulations containing the combination of a 2% solution of CCA-C and 0.1%, 0.25%, 0.5%, 1.0%, 2.0% and 4.0% of a dispersion of tetrachloroisophthalonitrile (the dispersion containing 40% active ingredient) are prepared by post adding the chloroisophthalonitrile dispersion to the CCA in water.

The formulations are examined for pH, color and appearance, initially and after 8 weeks aging at room temperature. The resulting data are set forth in Table 1. Also shown in the Table are the results for a 2% solution of CCA-C without tetrachloroisophthalonitrile addition (Control).

These formulations, as well as the Control sample, are tested for mildew resistance using potato dextrose agar inoculated with *Aspergillus niger* and incubated under the conditions shown in Table 2. Attention is invited to Table 2 for the data obtained.

TABLE 1

| | Example 1 - Stability Data | | | | | |
|---|---|---|---|---|---|---|
| | Color | | pH | | Appearance* | |
| | Initial | 8 Wks. @ R.T. | Initial | 8 Wks. @ R.T. | Initial | 8 Wks. @ R.T. |
| Control | Orange | Orange | 2.3 | 2.3 | No separation | No separation |
| 0.1% | Orange | Orange | 2.4 | 2.4 | Separation | Separation |
| 0.25% | Lt. Yellow | Lt. Yellow | 2.3 | 2.4 | Separation | Separation |
| 0.5% | Lt. Yellow | Lt. Yellow | 2.4 | 2.4 | Separation | Separation |

TABLE 1-continued

| | Example 1 - Stability Data | | | | | |
|---|---|---|---|---|---|---|
| | Color | | pH | | Appearance* | |
| | Initial | 8 Wks. @ R.T. | Initial | 8 Wks. @ R.T. | Initial | 8 Wks. @ R.T. |
| 1.0% | Yellow | Yellow | 2.4 | 2.5 | Separation | Separation |
| 2.0% | Yellow | Yellow | 2.5 | 2.5 | Separation | Separation |

*Settling is seen in all samples containing tetrachloroisophthalonitrile after standing for 24 hours. However, the tetrachloroisophthalonitrile sediment is easily redispersed in all samples, with mild agitation. The addition of a suspending agent could be used to eliminate the settling. Foaming is observed initially and after aging (8 weeks at Room Temperature) in samples containing 2.0% & 4.0% of the dispersion of tetrachloroisophthalonitrile. The problem is eliminated with a small addition of defoamer.

TABLE 2

| | Example 1 - Mildew Resistance | | |
|---|---|---|---|
| | Rating* | Zone of Inhibition | Contact Area |
| | Incubation Period 7 days at 30° C.: | | |
| Control | 5 | 0 | + |
| 0.1% | 0 | 3 cm | — |
| 0.25% | 0 | 3 cm | — |
| 0.5% | 0 | 3 cm | — |
| 1.0% | 0 | 3 cm | — |
| 2.0% | 0 | 3 cm | — |
| | Incubation Period 14 days at 30° C.: | | |
| Control | 8 | 0 | + |
| 0.1% | 4 | 0 | + |
| 0.25% | 0 | 3 cm | — |
| 0.5% | 0 | 3 cm | — |
| 1.0% | 0 | 3 cm | — |
| 2.0% | 0 | 3 cm | — |

*Legend: Mildew Growth
0 — No growth
2 — Very slight growth
4 — Slight growth
6 — Moderate growth
8 — Moderate to heavy growth
10 — Heavy growth

EXAMPLE 2

7.0 Liters (237 fl.oz.) of MOLD-EX® is added to 22,700 gal. of CCA treating solution (1.1% CCA-C oxide, temperature 76° F.) to form a 0.01% MOLD-EX® dispersion in the treating solution (contents 40 ppm A.I. MOLD-EX®). MOLD-EX® is a 40.4% concentrate of tetrachloroisophthalonitrile as the active ingredient, available from Mineral Research & Development Corporation. The CCA treating solution is formed from CCA-C.

The lumber treated is Southern pine (14% moisture, 14% heartwood, 2×4's & 2×6's, total 23,145 board feet, 1318 ft.³). The lumber is treated by a pressure vacuum method of applying CCA wood preservative by the standard procedure prescribed by the American Wood Preservers Association to deposit on the lumber surface 156 ppm A.I. MOLD-EX®, based on retention of 3.2 gal./ft.³ of treating solution designed to give 0.4 lbs./ft.³ of CCA-C oxide retention.

EXAMPLE 3

20,944 gal. of a CCA treating solution (1.1% CCA-C oxide, temperature 76° F.) containing 0.025% of MOLD-EX® dispersed therein (100 ppm A.I. MOLD-EX®), is prepared by adding 10.75 liters of MOLD-EX® to a CCA treating solution already having present therein 5.4 liters of MOLD-EX®. Using the pressure vacuum method followed in Example 2, a lumber charge made up of Southern pine (13% moisture, 14% heartwood, 2×4's and 2×6's, total 24,300 board feet, 1374 ft.³) is treated to deposit on the lumber surface 392 ppm A.I. MOLD-EX ®, based on retention of 3.2 gal./ft.³ of treating solution designed to give 0.4 lbs./ft.³ of CCA-C oxide retention.

EXAMPLE 4

19,603 gal. of a CCA treating solution (1.1% CCA-C oxide, temperature 74° C.) containing 0.05% of MOLD-EX ® dispersed therein (200 ppm A.I. MOLD-EX ®), is formulated by the addition of 18 liters of MOLD-EX ® to a CCA treating solution already containing 12.23 liters of MOLD-EX ®. Employing the pressure vacuum method used in Example 2, a lumber charge of face coverage was evident on wood pieces taken throughout the lumber stacks. Tetrachloroisophthalonitrile, which is used as a dispersion, did not penetrate the wood as does CCA-C, a solution. Surface deposition of the fungicide is desirable because the problem molds occur predominately on wood surfaces. It is apparent that this application method gives adequate fungicide surface coverage for control of problem mold organisms.

The above Examples are illustrative of the present invention. It is to be understood that these examples are not in any way to be interpreted as limiting the scope of the invention. Rather, it is intended that the scope of the invention be defined by the claims set forth below.

TABLE 3

| ANALYSIS OF TREATING SOLUTION SAMPLE | | | EVALUATION OF LUMBER BUNDLES | | | | |
|---|---|---|---|---|---|---|---|
| | CCA—C Oxide | MOLD-EX ® A.I.³ | % Covered by Mold % (Avg) | Range | % Boards with Mold | General Comment | Bundle Interior |
| Example 2 | 1.115% | 23.3 ppm⁴ | | | | | |
| Covered | | | <1 | <1-<1 | 30% | Very clean | Slight mold |
| Uncovered | | | <1 | 1-1 | 15% | Very clean | Slight mold |
| Example 3 | 1.139%¹ | 24.8 ppm⁵ | | | | | |
| Covered | | | <1 | <1-<1 | 37.5% | Exceptionally clean | Very slight occurrence |
| Uncovered | | | 0 | | 0 | Exceptionally clean | Very slight occurrence |
| Example 4 | 1.139%² | 51.7 ppm⁵ | | | | | |
| Covered | | | <1 | <1-<1 | 15% | Clean | Same as general comment |
| Uncovered | | | 0 | | 0 | Exceptionally clean | Same as general comment |
| UNTREATED | approx. 1.1% | 0 | | | | | |
| Covered | | | 5 | 1-10 | 80% | Clean, faint black smudges | Same as general comment |
| Uncovered | | | 50 | 10-80 | 100% | Spotted, distinct mold under inoculating board | Same as general comment |

¹Average of two samples.
²Average of three samples.
³The MOLD-EX ® A.I. is dispersion. Therefore, particles filter out on wood surface. Thus, the amount of A.I. present in treating solution at start is expected to be higher than at the end of treatment.
⁴Sample taken during treatment.
⁵Sample taken at end of treatment.

Southern pine (13% moisture, 14% heartwood, 2×4's, total 23,760 board feet, 1318 ft.³) is treated to deposit on the lumber surface 783 ppm A.I. MOLD-EX ®, based on retention of 3.2 gal./ft.³ of treating solution designed to give 0.4 lbs./ft.³ of CCA-C oxide retention.

The treated lumber bundles of Examples 2–4, and, for comparison, untreated lumber bundles are left outdoors to weather for approximately 4 months, 1 week, after which an evaluation is made. All bundles are provided prior to the test period, with an inoculating board on top. The inoculating boards appear to be similarly infested with one or more of the following fungal species: *Aspergillus flavus, Asperqillus niger, Penicillium expansum, Pullularia pullulans* and *Trichoderma sp.* Each treatment during the test period has lumber bundles covered with polyethylene and uncovered lumber bundles, with a polyethylene covering being provided and no covering being used for the untreated bundles also. The results of the evaluation are shown in Table 3.

Furthermore, the treated wood surfaces were visually examined for location and distribution of the tetrachloroisophthalonitrile by exposing the wood to ultra violet (UV) light, which excites the compound to a visible state. It appeared that surfaces were lightly covered, although more was deposited on top surfaces than on underneath (bottom), which was anticipated with a dispersion application system. The same degree of sur-

I claim:
1. A wood-treating composition useful for the preventive control of surface molds and as a wood preservative, consisting essentially of a concentration of chromated copper arsenate effective as a wood preservative when applied to wood, and an amount of a chemically compatible, halogenated benzene dinitrile effective to protect wood against surface molds when applied to wood, said amount being at least about 40 ppm, and the benzene dinitrile being of the general formula

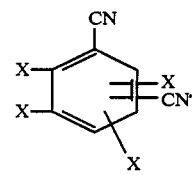

wherein each X is selected from the group consisting of hydrogen, chlorine, fluorine and bromine, with at least one X being other than hydrogen; and said wood-treating composition being free of working solution sludge caused by reaction between said halogenated benzene dinitrile and said chromated copper arsenate.

2. The composition of claim 1, formed with respect to the wood preserving ingredient, from an about 50% concentrate of chromated copper arsenate containing as active ingredients, about 22.4% $CrO_3$, about 8.6% CuO, and about 19% $As_2O_5$.

3. The composition of claim 1, wherein the benzene dinitrile is tetrachloroisophthalonitrile.

4. The composition of claim 1, wherein said amount of the benzene dinitrile ranges from about 40 ppm up to and including about 16,000 ppm.

5. The composition of claim 1, wherein said amount of the benzene dinitrile ranges from about 40 ppm up to and including about 400 ppm.

6. Treated wood having applied thereto an amount of chromated copper arsenate effective as a wood preservative, and having applied in direct surface contact with the surface of the wood, an amount of a chemically compatible, halogenated benzene dinitrile effective to protect against surface molds, the benzene dinitrile being deposited from a composition comprising at least 40 ppm thereof and the benzene dinitrile being of the general formula

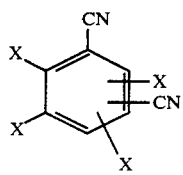

wherein each X is selected from the group consisting of hydrogen, chlorine, fluorine and bromine, with at least one X being other than hydrogen; said treated wood being free of precipitate deposits caused by reaction between said halogenated benzene dinitrile and said chromated copper arsenate.

7. The treated wood of claim 6, having on the order of about 150 to 780 ppm of said benzene dinitrile applied thereto.

8. The treated wood of claim 6, wherein said benzene dinitrile is tetrachloroisophthalonitrile.

9. The treated wood of claim 6, wherein the chromated copper arsenate is CCA-C.

10. The treated wood of claim 6, wherein the wood is lumber.

11. The treated wood of claim 10, wherein the lumber is Southern pine.

12. The treated wood of claim 6, wherein the wood is fresh-cut or unseasoned wood.

13. The composition of claim 1, comprising about 1.1% to 2% active ingredient CCA-C as said chromated copper arsenate.

14. The composition of claim 1, useful for the preventive control of *Pullularia pullulans*.

15. The treated wood of claim 6, having applied thereto an amount of said halogenated benzene dinitrile effective to protect against *Pullularia pullulans*.

16. A composition consisting essentially of about 1.1% to 2% active ingredient CCA-C, and from about 40 ppm up to and including about 16,000 ppm of a chemically compatible, halogenated benzene dinitrile, the benzene dinitrile being of the general formula

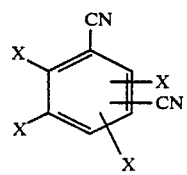

wherein each X is selected from the group consisting of hydrogen, chlorine, fluorine and bromine, with at least one X being other than hydrogen; and said composition being free of working solution sludge caused by reaction between said halogenated benzene dinitrile and said CCA-C.

* * * * *